United States Patent [19]
Failla et al.

[11] Patent Number: 5,382,252
[45] Date of Patent: Jan. 17, 1995

[54] TRANSVAGINAL UTERINE MANIPULATOR

[75] Inventors: Stephen J. Failla, Cincinnati; Patrick J. Traini, Bellbrook; Charles M. Rarey, Cincinnati, all of Ohio

[73] Assignee: Ethicon Endo-Surgery, Cincinnati, Ohio

[21] Appl. No.: 217,266

[22] Filed: Mar. 24, 1994

[51] Int. Cl.6 .............................................. A61B 17/00
[52] U.S. Cl. ...................................... 606/119; 128/17
[58] Field of Search ................. 128/3, 17, 20; 604/55, 604/164–170, 264, 282; 606/1, 108, 119, 190–193, 198

[56] References Cited

U.S. PATENT DOCUMENTS

| | | |
|---|---|---|
| 2,482,622 | 9/1949 | Kahn . |
| 3,809,091 | 5/1974 | Shute . |
| 3,877,433 | 4/1975 | Librach . |
| 4,000,743 | 1/1977 | Weaver ................................ 606/119 |
| 4,022,208 | 5/1977 | Valtchev . |
| 4,089,337 | 5/1978 | Kronner . |
| 4,775,362 | 10/1988 | Kronner ................................ 604/96 |
| 4,997,419 | 3/1991 | Lakatos et al. ...................... 604/55 |
| 5,100,382 | 3/1992 | Valtchev ............................. 604/96 |
| 5,195,964 | 3/1993 | Kletzky et al. ..................... 604/55 |
| 5,217,466 | 6/1993 | Masson ............................... 606/1 |
| 5,237,985 | 8/1993 | Hodgson et al. ................... 606/119 |

*Primary Examiner*—Stephen C. Pellegrino
*Assistant Examiner*—Glenn Dawson

[57] ABSTRACT

An improved transvaginal uterine manipulator is disclosed. In the most preferred embodiment, it has an elongated housing, a releasable tip attached to the distal end of the housing, a handle lever to actuate means for pivoting the tip in anteversion and retroversion motions in such a manner that a direct positional relationship between the handle lever and tip exists, an arcuate tip position indicator, a tenaculum holder attached to the housing, a constant force spring attached within the elongated housing and to the holder for applying a constant force on a tenaculum held by the holder regardless of its position on the housing, a handle lever locking means to lock the position of the handle, and fluid delivery means through the tip to deliver fluid to the uterus.

5 Claims, 5 Drawing Sheets

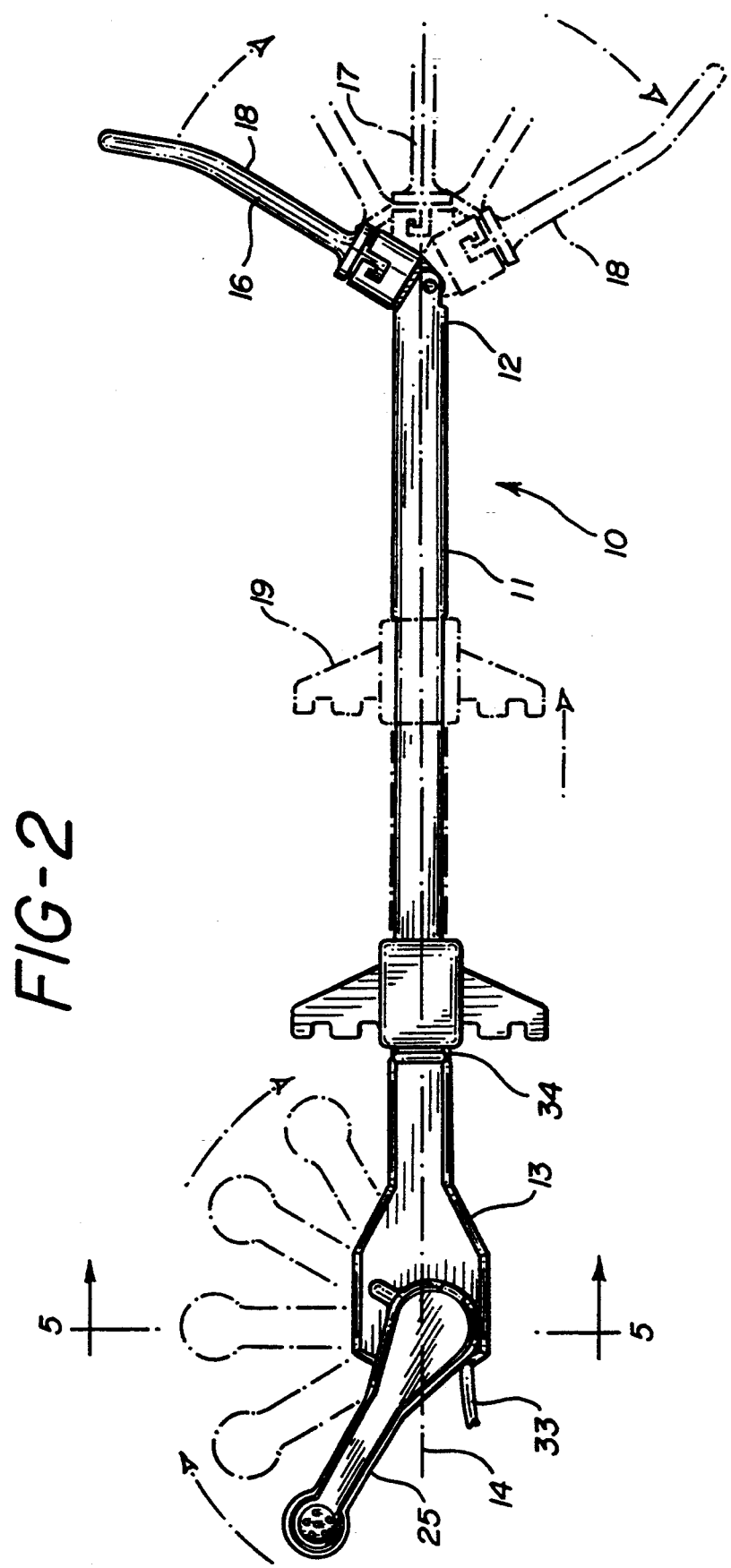

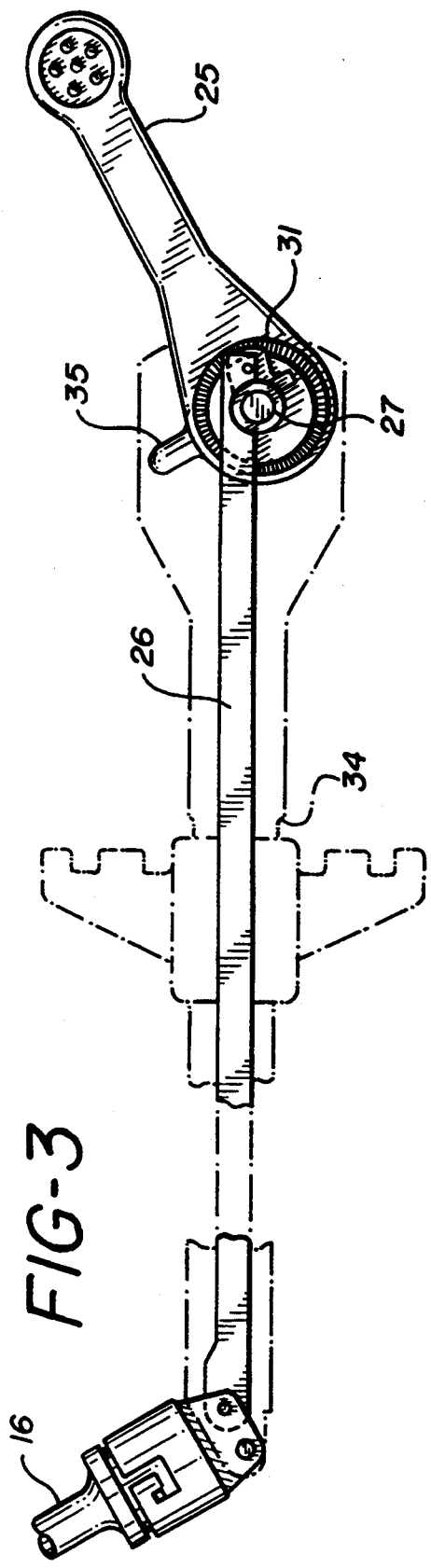
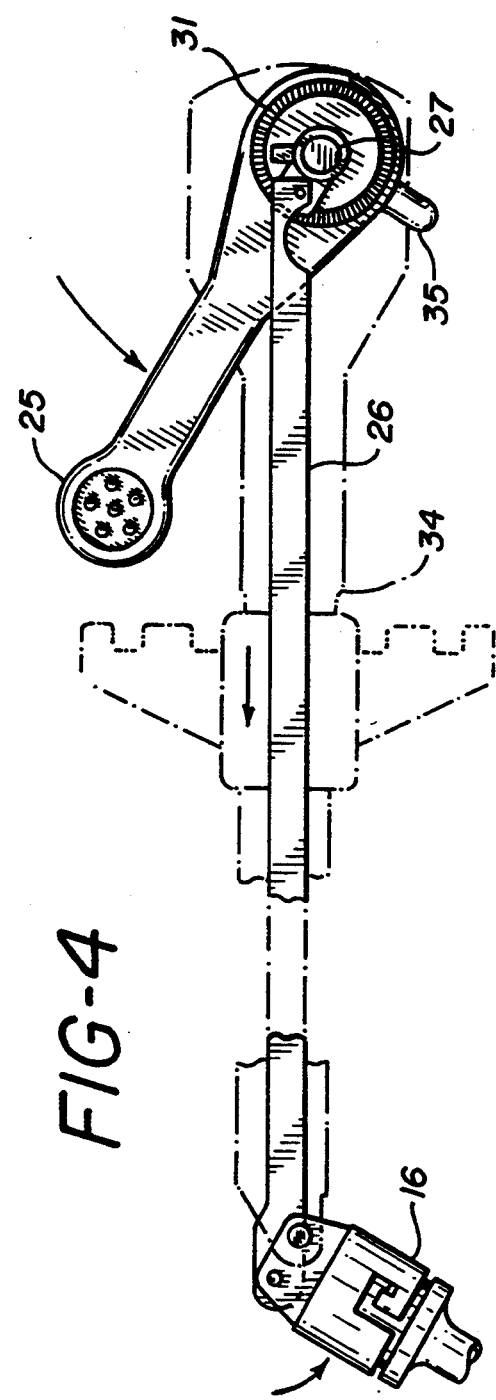

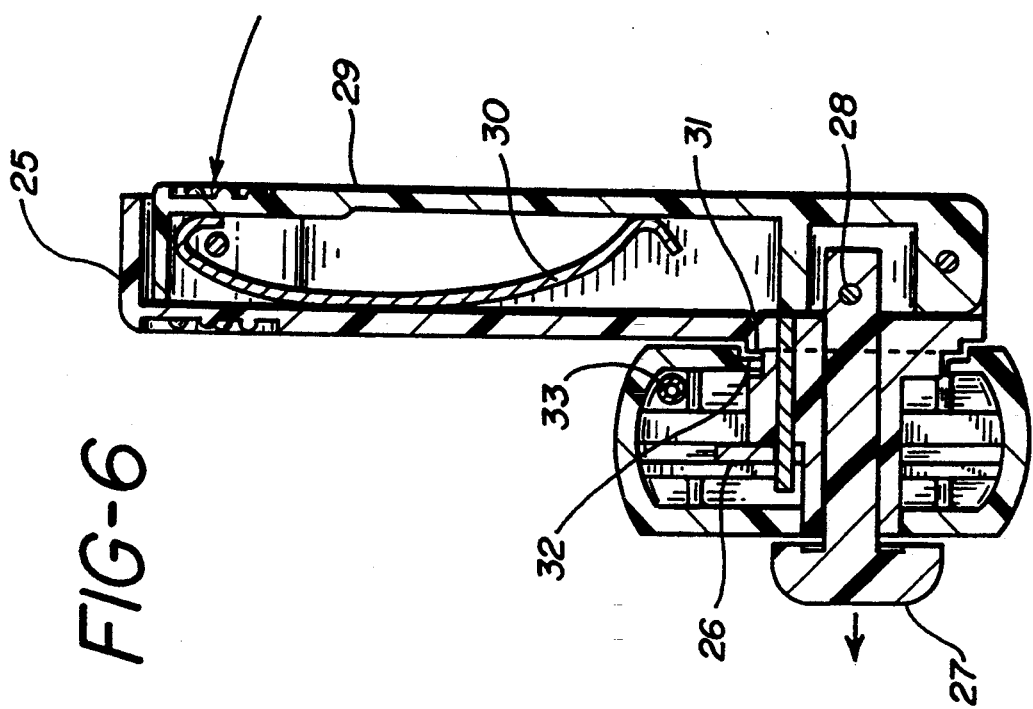
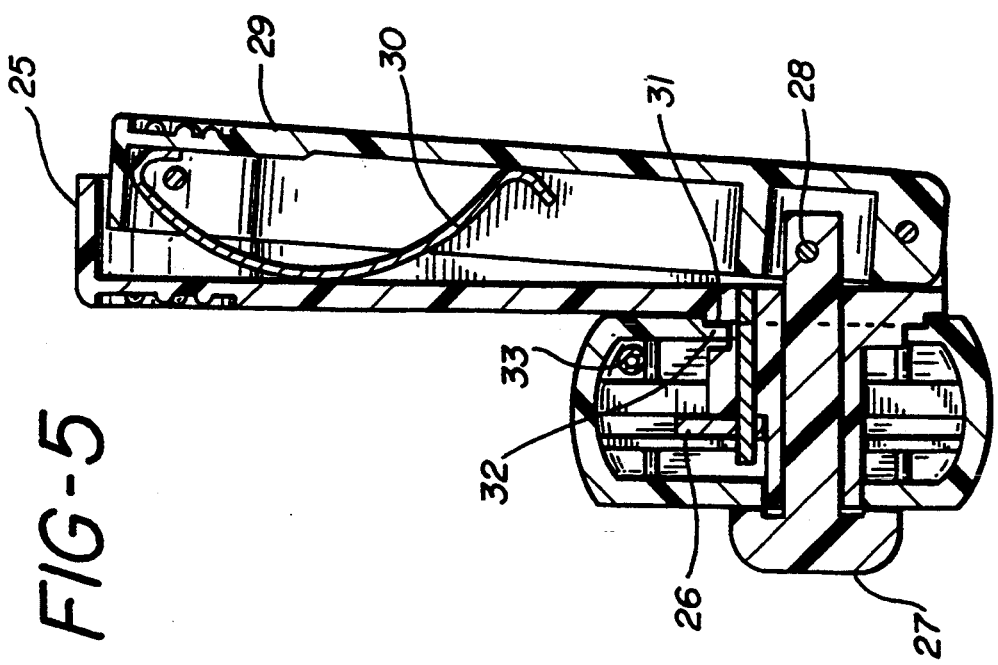

TRANSVAGINAL UTERINE MANIPULATOR

BACKGROUND OF THE INVENTION

This invention relates generally to a transvaginal uterine manipulator. More specifically, it relates to a transvaginal uterine manipulator having an improved tenaculum holder, tip, and handle lever control.

Transvaginal uterine manipulators are medical instruments used to manipulate a patient's uterus during gynecological surgical and diagnostic procedures. Such procedures include dye or radio-opaque liquid injection for fallopian tube patency examination, biopsy tissue collection, and any of numerous open and laparoscopic surgical and diagnostic procedures.

The movement toward laparoscopic gynecologic surgery has generated an awareness and a need for a better uterine manipulator. Previous laparotomy procedures through the abdominal wall provided easy access for traditional manipulation devices. Laparoscopic procedures through small incisions using trocars in the lower pelvic region are constrained by the anatomical boundary conditions such as patient's size, blood vessels, pelvic bones, etc. These boundary conditions restrict the number of trocar ports used in the laparoscopic procedure and their locations. Due to restrictions and cost constraints, the gynecology surgeon will take advantage of the natural operative port—the vagina and uterus. The natural port requires the use of different instrumentation from other laparoscopic tissue manipulators. It requires the use of uterine manipulators with specific features which are not generally found in current instruments available to the gynecologic surgeon. Recent market surveys indicate that nearly all laparoscopic gynecological procedures will utilize a uterine manipulator.

Current uterine manipulators are typified by that described by Valtchev in U.S. Pat. No. 4,022,208. This device allows manipulator movement in one direction only, allows fluid to be dispensed through the tip, and provides a tenaculum holder with a compression spring to apply force to a tenaculum, as well as a cervical sealing surface on the tip. A tenaculum is a forceps instrument which at its distal end is used to grasp the neck of the cervix and by attaching the proximal end of the tenaculum to the manipulator housing, axial force is applied on the tenaculum in the proximal direction to retain the manipulator tip in its position within the uterus. In another Valtchev patent, U.S. Pat. No. 5,100,382, a different means for providing a sealing surface on the tip of the manipulator is described. The interchangeable tip employs the use of an inflatable balloon to provide the requisite sealing.

Other examples of uterine manipulators abound. U.S. Pat. No. 4,089,337 describes a manipulator with an inflatable tip section which is used along with an adjustable spring-loaded disc to seal the cervix. An earlier patent, U.S. Pat. No. 2,482,622, shows many of the features found in uterine manipulator instruments used today, such as: tenaculum holder which is moveable but when in use is rigidly fixed, sealing surface on the manipulator tip, interchangeable tips, and ability to rotate the tip in one direction. The following additional references also describe various uterine manipulators: U.S. Pat. Nos. 4,775,362; 3,877,433; and 3,809,091.

All of the above devices are acceptable and their features are found on instruments used today. However, certain shortcomings are important to overcome. For example, none of these instruments provide a means to apply a constant tensile force on the tenaculum, regardless of the precise positioning of the tenaculum on the tenaculum holder of the manipulator instrument. A constant force on the tenaculum would in turn provide a constant reaction force on the cervix during continued adjustment of the manipulator position. This constant force feature is important in that it provides a constant insertion force on the manipulator tip to retain the tip within the uterus at all times during the procedure and to prevent it from sliding out of position. Additionally, when using the manipulation for liquid injection, the equivalent force provides a reliable hermetic seal between the mouth of the cervix and the cervical sealing surface of the tip. The Valtchev design using a compression spring for this function is subject to the problem of greatly varying force on the tenaculum which depends upon the amount of deflection applied to the compression spring. This results in an uncontrollable and unknown amount of force relied upon to hold the manipulator tip in the uterus. This uncontrollable force may also result in leakage of any medical fluid injected through the manipulator which may be required to determine tubal patency or to deliver medications.

Additionally, none of the current devices provide a direct angular motion relationship between the handle activation lever and the tip movement or an indicator to communicate this relationship to the user. This feature is important to allow the surgeon to know exactly where the tip is positioned at all times even when the manipulator is not visible because it may be located under surgical drapes during the procedure. Some of these devices possess the feature of the handle remaining in a locked position when the surgeon adjusts the handle to the desired position during the procedure, however, the adjustment requires two hands for its accomplishment. The surgeon does not desire the tip position to change relative to the instrument without the surgeon's control.

Accordingly, in the view of the deficiencies of existing uterine; manipulators, what is needed is a uterine manipulator incorporating new features to better serve the gynecological surgeon's needs. Specifically, what is truly desired is a manipulator capable of providing a constant force on the tenaculum regardless of the positioning of the tenaculum in its holder on the manipulator. Additionally, it would be desirable to provide a manipulator where the handle actuation lever can be easily locked into a desired position using only one hand, and that position be clearly indicated as a reliable indication to the surgeon of the corresponding positioning of the tip of the uterine manipulator.

SUMMARY OF THE INVENTION

The present invention is an improvement to the conventional instrument for manipulation of a patient's uterus during a gynecological surgical or diagnostic procedure. The conventional uterine manipulator generally has an elongated housing with a distal and proximal end and a longitudinal axis, a releasably attached tip at the housing distal end for positioning the uterus of a patient, actuation means attached to the housing proximal end for pivoting the tip from a first position parallel to the longitudinal axis to a second position, and a slidable tenaculum holder on the elongated housing for attaching a tenaculum to grip and hold the patient's cervix. The improvements to the conventional manipulator to which this invention specifically relates comprise means for applying a constant axial pulling force on the tenaculum holder toward the housing proximal end to cause a constant tension on the patient's cervix when the holder attaches the tenaculum to grip and hold the patient's cervix, and preferably one-handed motion of the handle lever to move and lock the tip in the desired position, as well an indicator to communicate the tip position to the surgeon.

The most preferred means for applying the constant axial force on the tenaculum holder is to use the desirable features of a constant force spring which is attached within the manipulator housing proximal end at one end and to the tenaculum holder at its other end to apply a constant tension to the tenaculum. The tenaculum grips and holds the patient's cervix throughout the range of manipulator motion which normally occurs during the surgical procedure. This constant tension on the tenaculum and consequently the patient's cervix while the surgeon is maneuvering the manipulator during the surgical procedure will cause an equal reaction force in the opposite axial direction on the manipulator resulting in a constant insertion force on the manipulator tip. This constant tip insertion force will insure that the tip will remain in its most effective functioning position in the patient's uterus and will not inadvertently slide out during the surgical procedure. This feature is important to enable the surgeon to perform both the surgical and diagnostic procedure more efficiently.

The constant force feature of the present invention is important for improving another aspect of a surgical procedure. Medical fluids are frequently dispensed through the manipulator tip at various times during the procedure and the fluids are retained in the uterus by the sealing effect of a shoulder on the manipulator tip pressing against the cervix opening. When this shoulder either loses contact or the contact force is reduced, the diagnostic examination fluids are inadvertently lost. The constant force improvement of this invention will cause the tip shoulder to be in constant contact with the patient's cervix and assure adequate sealing of the medical fluids dispensed into the uterus.

Another improvement of the present invention is the incorporation of a direct arcuate motion relationship between the manipulator handle lever and the tip. When the handle lever is in a position perpendicular to the longitudinal axis of the manipulator, the tip is in line with the longitudinal axis. This position would normally be chosen for insertion of the tip into the uterus. After tip insertion, the distal end of the tenaculum would be clamped onto the cervix and the proximal end attached to the tenaculum holder with the tenaculum positioned along the longitudinal axis of the manipulator. Next, the manipulator handle lever can be rotated to any of several incremental angular positions to approximately 60 degrees either proximally toward the surgeon which will force the tip in the same upward or anteverted direction by the same angular displacement, or distally away from the surgeon which will force the tip in the same downward or retroverted direction. As part of this improvement, visual arcuate position indicators are attached to the handle and to the clamp opposed to the handle. The indicators always point in the direction parallel to the tip. The indicators point the direction of the tip. The indicators always point in the direction parallel to the tip. This improvement is important to the surgeon because the tip is not visible during the surgical procedure and by moving the handle lever the desired amount and direction, the surgeon is assured that the tip has the same direction and arcuate position. Also, these improvements become even more important when the manipulator must be operated when it is covered by surgical drapes and may not be visible to the surgeon or assistant. In this situation, the surgeon can still receive tactile feedback from the handle position while manipulating the instrument will indicate the tip position at any time during the procedure.

Another improvement of the present invention is the incorporation of a releasable locking mechanism on the handle lever. This mechanism provides a locking feature to the instrument such that when the handle lever is squeezed the handle is unlocked. Then it can be rotated to place the tip in its desired position for the surgical procedure. The handle lever is then released and the handle lever becomes stationary in that position and consequently, the tip remains in its desired position. This improvement is important because adjustment can be accomplished rapidly and conveniently with one hand even when the instrument is under surgical drapes. Any undesirable tip movement during a surgical procedure would be a problem to the surgeon, and thus this improved feature substantially eliminates or reduces the severity of this problem.

The transvaginal uterine manipulator of this invention can be used during any gynecological surgical or diagnostic procedure which requires the positioning of the uterus of the patient and for liquid medicine injections.

BRIEF DESCRIPTION OF THE DRAWINGS

FIG. 2 is a side elevational view of the transvaginal uterine manipulator showing the range of motion of the handle and tip and the tenaculum holder.

FIGS. 3 and 4 are partial elevational views of the transvaginal uterine manipulator showing the relationship of the handle and tip and their movement.

FIG. 5 is a cross sectional view of the body and handle of the transvaginal uterine manipulator shown in the locked position as taken along line 5—5 of FIG. 2.

FIG. 6 is a cross sectional view of the body and handle of the transvaginal uterine manipulator shown with the handle unlocked.

DETAILED DESCRIPTION OF THE INVENTION

Figure 1:
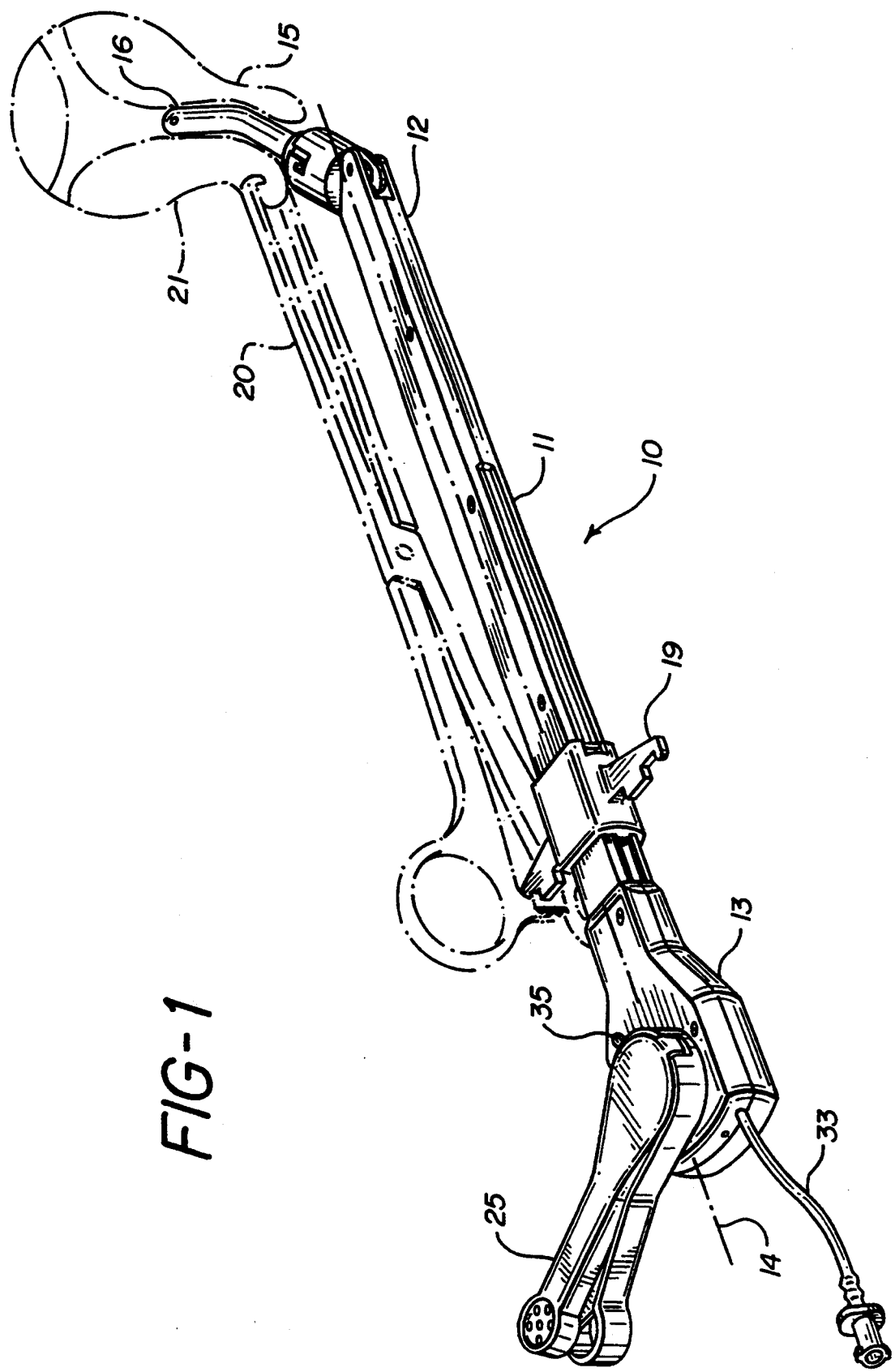
FIG. 1 is a perspective view of the transvaginal uterine manipulator as seen from the bottom and right side.

Referring now to FIG. 1, there is shown the preferred embodiment of the transvaginal uterine manipulator 10. The manipulator 10 has an elongated housing 11. The housing 11 has two ends, a distal end 12 and a proximal end 13. The distal end 12 and proximal end 13 of the housing 11 are disposed along a longitudinal axis 14.

The purpose of the transvaginal uterine manipulator 10 is for the surgeon to control the orientation of the female uterus 15 in order to perform a surgical or diagnostic procedure. Contact with the uterus 15 is made using a movable tip 16. The tip 16 is releasably attached to the distal end 12 of the manipulator housing 11. Releasing the tip and attaching another one is necessary to allow use of different shapes to accommodate normal anatomical variations in the female uterus and to provide a passage for injecting medical fluids when desired. The tip 16 is activated from the proximal end 13 of the manipulator 11. The range of motion of tip 16 varies from a first position 17 parallel to the longitudinal axis 14 to a second position 18. FIG. 2 shows the position ranges of tip 16.

The transvaginal uterine manipulator 10 includes a tenaculum holder 19 which is used to hold a tenaculum 20 and apply an axial force to the cervix 21 of the patient. The tenaculum 20 and cervix 21 are shown in outline format in FIG. 1. The application of a constant axial force to the cervix 21 through the manipulator 10 is necessary so that the tip 16 will not be dislodged when the surgeon maneuvers the uterus 15 during the surgical procedure.

Figure 7:
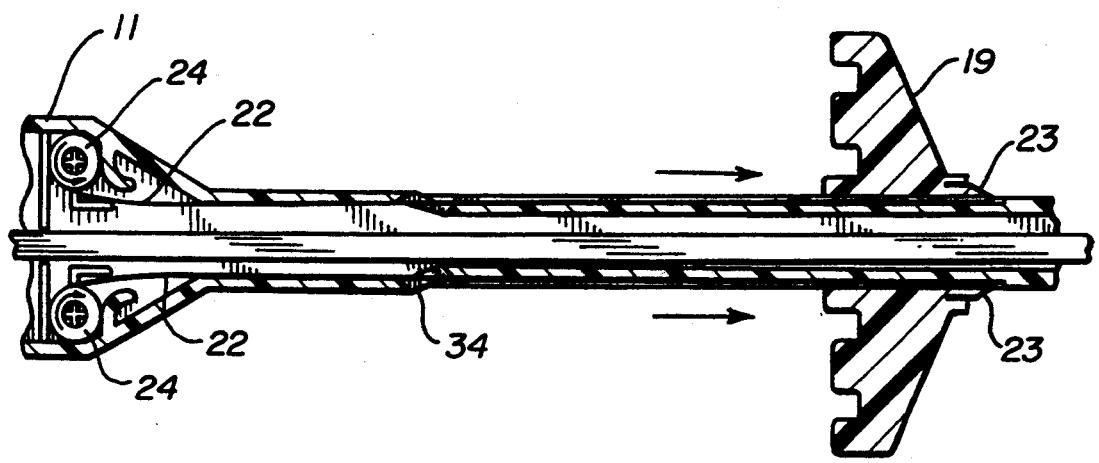
FIGS. 7 and 8 are partial cross sectional views of the transvaginal uterine manipulator showing the movement of the tenaculum holder and the constant force spring.
Figure 8:
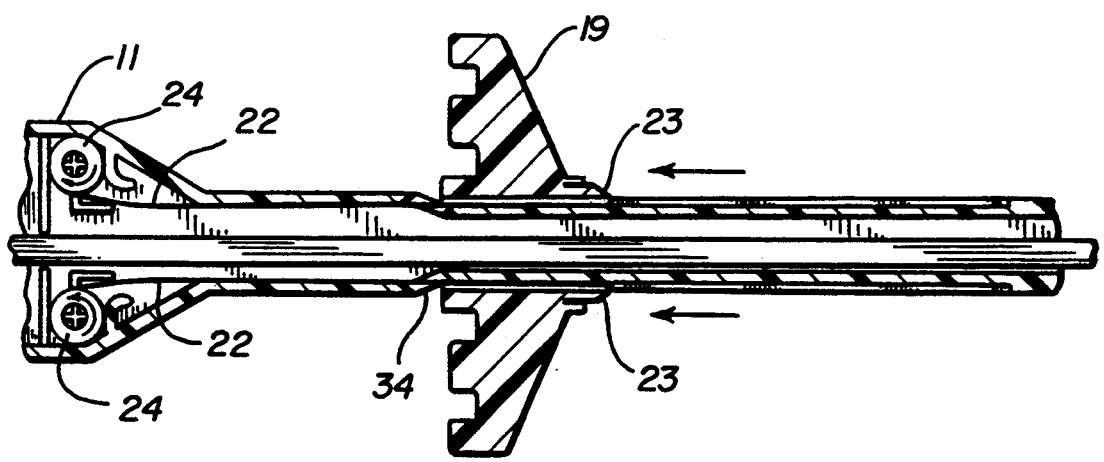

The constant axial force on the cervix 21 is provided using constant force springs 22 shown in FIGS. 7 and 8. The nature of this type of coiled flat metal spring 22 is to provide a constant force tending to cause the extended coils to return to their non-extended condition. This force condition exists at essentially any extended spring length. The constant force springs 22 are attached to the slidable tenaculum holder 19 at their free ends 23, and their coiled ends 24 are retained in the manipulator housing 11. The particular configuration of the design of the housing illustrated in FIGS. 7 and 8 makes it unlikely that the spring would inadvertently, catch the surgeon's gloves, drapes, or other instrumentation during the surgical procedure. FIG. 7 shows the slidable tenaculum holder 19 extended along manipulator housing 11 with the constant force spring 22 extended. FIG. 8 shows the slidable tenaculum holder 19 retracted by the constant force spring 22 and resting against the stop 34 on the manipulator housing 11.

The tip 16 is actuated from the proximal end 13 of the manipulator housing 11 through movement of handle lever 25. Handle lever 25 is rotatably mounted in the manipulator housing 11 using clamp 27 and 28 as shown in FIGS. 5 and 6. A control link 26 connects the handle lever 25 to the tip 16 as shown in FIGS. 3 and 4. With the linkage 26 shown, the tip 16 moves in a direct arcuate relationship to the arcuate movement of the handle lever 25. Position indicator 35 as shown on FIGS. 2, 3 and 4 on handle lever 25 is positioned to be always pointing in a direction parallel to the direction of the tip 16.

A one handed releasable locking mechanism for handle lever 25 is shown in FIGS. 3 through 6. An unlocking arm 29 of handle lever 25 contains a leaf spring 30. Handle lever 25 includes an array of radially oriented detents 31 on its surface. A matching array of radially oriented detents 32 are on the manipulator housing 11. With the transvaginal uterine manipulator 10 at rest, the leaf spring 30 forces the handle lever detents 31 to mesh with the manipulator housing detents 32 causing the handle lever 25 to be in a locked position. The locked position is shown in FIG. 5. When the handle lever 25 and unlocking arm 29 are squeezed together, the unlocking arm 29 pivots about pin 43 in an arcuate motion shown in FIG. 6. The arcuate motion causes clamp 27 to move axially, disengaging the detent arrays 31 and 32 unlocking the handle lever 25. In this manner, the handle lever 25 can be rotated to move the tip 16 to the desired position by the surgeon. Once in the desired position, the surgeon releases the squeezing motion on handle lever 25 and unlocking arm 29, causing the handle lever 25 to be locked in its desired position.

The transvaginal uterine manipulator 10 in the preferred embodiment has a fluid dispensing channel 33 which extends through the manipulator housing 11 to dispense fluids through the tip 16.

This invention has been described with respect to its most preferred embodiment. However, the reader should realize that numerous additional embodiments are contemplated within the scope of this invention as it is defined by the appended claims.

What is claimed is:

1. A transvaginal uterine manipulator of the type having an elongated housing having distal and proximal ends and a longitudinal axis, a tip releasably attached at said housing distal end for positioning a uterus of a patient, a handle lever rotatably mounted to said housing proximal end and a control linkage connecting said handle lever to said tip for pivoting said tip from a first position parallel to said longitudinal axis to a second position when said handle lever is rotated, and a tenaculum holder slidable on said elongated housing for attaching a tenaculum having proximal and distal ends to grip and hold said patient's cervix; wherein the improvement comprises:
    a) means for applying a constant axial pulling force on said tenaculum holder toward said housing proximal end thereby causing a constant tension on said patient's cervix when said holder engages said tenaculum proximal end and said tenaculum distal end is attached to grip and hold said patient's cervix,
    b) means for indicating arcuate position of said tip at said housing proximal end,
    c) a connection between said handle lever and said control linkage connecting said handle lever to said tip wherein arcuate rotation of said handle lever produces substantially identical arcuate pivoting motion to said tip, and
    d) locking means comprising an unlocking arm pivotally attached to said handle lever for selectively maintaining or releasing said handle lever from a locked pivoted position relative to said housing longitudinal axis.

2. The manipulator of claim 1 wherein said means for applying a constant axial pulling force on said tenaculum holder is a constant force spring having a first end attached within said housing proximal end and a second end attached to said slidable tenaculum holder.

3. The manipulator of claim 2 wherein said locking means further first plurality of detents displayed on said handle lever; a second plurality of detents displayed within said elongated housing proximal end, said first and second plurality of detents positioned in intermeshing relationship so as to lock said handle lever in said locked pivoted position; a leaf spring displayed within said handle lever for firmly maintaining said handle lever in said locked pivoted position; and disengaging means for disengaging said first and second plurality of detents so as to release said handle lever from said locked pivoted position.

4. The manipulator of claim 3 wherein said disengaging means includes opposed squeezing surfaces displayed on said handle lever and said unlocking arm whereby said leaf spring is deflected to disengage said first and second plurality of detents when said squeezing surfaces are squeezed.

5. The manipulator of claim 1 wherein said tip has a fluid dispensing channel therethrough so as to allow transport of fluids through said tip.

* * * * *